United States Patent [19]

Pugia et al.

[11] Patent Number: 5,631,163

[45] Date of Patent: May 20, 1997

[54] METHOD FOR THE DETERMINATION OF SPECIFIC GRAVITY OF FLUIDS

[75] Inventors: Michael J. Pugia, Granger; Rena A. Ide, Elkhart, both of Ind.

[73] Assignee: Bayer Corporation, Elkhart, Ind.

[21] Appl. No.: 546,904

[22] Filed: Oct. 23, 1995

[51] Int. Cl.$^6$ .................................................. G01N 31/00
[52] U.S. Cl. ........................... 436/2; 436/74; 436/163; 436/169; 422/56; 435/287.7; 73/32 R
[58] Field of Search ........................... 436/2, 169, 163, 436/74; 422/55, 56; 435/287.7; 73/32 R; 427/2.1, 2.11, 2.13

[56] References Cited

U.S. PATENT DOCUMENTS

| | | | |
|---|---|---|---|
| 4,318,709 | 3/1982 | Falb et al. | 436/163 |
| 4,376,827 | 3/1983 | Stiso et al. | 436/2 |
| 4,473,650 | 9/1984 | Wang | 436/2 |
| 4,532,216 | 7/1985 | Wang | 436/2 |
| 4,670,218 | 6/1987 | Gantzer et al. | 422/56 |
| 5,055,407 | 10/1991 | Lau et al. | 436/2 |
| 5,064,615 | 11/1991 | Mangold et al. | 422/56 |
| 5,302,531 | 4/1994 | Bauer | 436/74 |
| 5,320,969 | 6/1994 | Bauer et al. | 436/84 |
| 5,350,694 | 9/1994 | Zimmerle | 436/2 |
| 5,403,744 | 4/1995 | Zimmerle | 436/2 |

*Primary Examiner*—Jill Warden
*Assistant Examiner*—Maureen M. Wallenhorst
*Attorney, Agent, or Firm*—Jerome L. Jeffers

[57] ABSTRACT

Disclosed are a method and device for the determination of specific gravity in aqueous systems, particularly urine. The invention improves upon the known systems for detecting specific gravity by the use of a polyelectrolyte polymer and pH indicator by the addition of a crown ether ionophore which enhances the ability of the reagent system to indicate the fluid's specific gravity.

12 Claims, No Drawings

METHOD FOR THE DETERMINATION OF SPECIFIC GRAVITY OF FLUIDS

BACKGROUND OF THE INVENTION

The present invention relates to the determination of the specific gravity of a fluid test sample. The determination of the specific gravity of a fluid test sample has numerous practical applications in various fields such as brewing, urinalysis and water purification. Particularly in urinalysis, the determination of the kidney's ability to respond to variations in fluid intake can be made by measuring the urine's specific gravity since the specific gravity is a function of the number, density, ionic charge and weight of the various species of dissolved solutes. For example, it has been reported that for every incremental increase of 0.12M in NaCl concentration, a corresponding change in specific gravity of 0.005 occurs. Detection of increases in a patient's urine concentration of sodium would be of interest to the clinician as an indicator of risk of hypertension and the patient's dietary control.

A state of the art technique for the quick and inexpensive determination of the specific gravity (as a function of ionic strength) is disclosed in U.S. Pat. No. 4,318,709. This technique involves the use of a weakly acidic or basic polyelectrolyte polymer which is at least about 50 percent neutralized and an indicator which is capable of producing a detectable response to ion exchange between the polyelectrolyte and the fluid sample being tested. In U.S. Pat. No. 4,376,827 this technique is extended to strongly acidic and basic polyelectrolytes. In U.S. Pat. No. 4,670,218 there is disclosed a test means for determining the presence of an ion in an aqueous test sample which involves contacting the test sample with an ionophore and an indicator capable of interacting with the complex formed between the ionophore and ion to produce a detectable response. Exemplary of the ionophore used in this system are cyclic polyethers commonly referred to as crown ethers.

SUMMARY OF THE INVENTION

Disclosed is an improvement to the method for determining the specific gravity of a fluid test sample which method involves combining the test sample with an acidic or basic polyelectrolyte polymer which is at least about 50 percent neutralized and a pH indicator capable of detecting a change in pH due to ion exchange between the polyelectrolyte and the fluid test sample. The improvement involves introducing a crown ether ionophore into the combination of fluid sample, polymer and indicator.

DESCRIPTION OF THE INVENTION

The present invention is predicated on the discovery that the sensitivity of the test for specific gravity of aqueous fluids using a partially neutralized polyelectrolyte polymer and an indicator is increased by the inclusion of a crown ether ionophore in the test system. While the present invention is not predicated upon any mechanism or theory of operation, the improved sensitive may be the result of complexation of soluble salts by both the crown ether and the polyelectrolyte.

Polyelectrolytes suitable for use in the present invention include strongly acidic or basic polyelectrolytes such as poly(styrene sulfonic acid), poly(vinyl sulfuric acid), and poly(vinylbenzylammonium chloride). These electrolytes are normally employed in combination with a buffer capable of providing a pH of at least about 5.5 and an indicator as described in U.S. Pat. No. 4,376,827 which is incorporated herein by reference.

Preferred polyelectrolytes are those which are weakly basic or acidic such as are described in U.S. Pat. No. 4,318,709 (incorporated herein by reference) such as poly(acrylic acid), poly(maleic acid) maleic acid/vinylmethyl ether copolymer, poly(methacrylic acid), styrene/maleic acid copolymer, poly(vinylamine) and poly(4-vinylpyridine). Gantrez® S-97, a maleic anhydride/methylvinylether copolymer in its partially neutralized form is preferred for use as the polyelectrolyte due to its wide pKa range.

Regardless of the selection of polyelectrolyte, it should be at least about 50 percent neutralized to allow the release of protons causing a decrease in pH in response to salt cations. There is also included an indicator which is capable of producing a detectable response to ion exchange between the polyelectrolyte and the fluid sample which is typically urine. Suitable indicators include bromo thymol blue, alizarin, bromcresol purple, phenyl red and neutral red. Bromo thymol blue is a preferred pH indicator.

Crown ether ionophores suitable for use in the present invention include all macrocyclic polyethers containing oxygen donor atoms which are electron rich and which are capable of complexing with particular cations because of their molecular structure. Because of the unique sizes and geometries of particular crown ethers, they are adaptable to complexing with various ions. In so complexing the electron rich oxygen atoms in the crown ether orient towards the electron deficient cation while the carbon atom segments of the chain are simultaneously projected in a direction outwards from the cation to form a crown ether/cation complex which is charged in the center and hydrophobic at its perimeter.

Exemplary of crown ethers suitable for use in the present invention are dibenzo-16-crown-5-oxyacetic acid (hereafter crown A); dicyclohexano-16-crown-5-oxyacetic acid (hereafter crown B) and naptho-5-crown-5 (hereafter crown C).

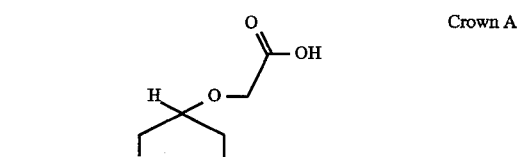

Crown A

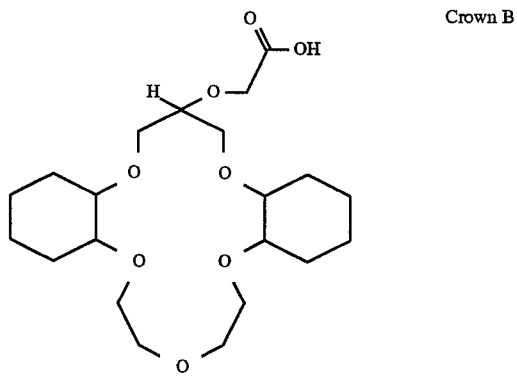

Crown B

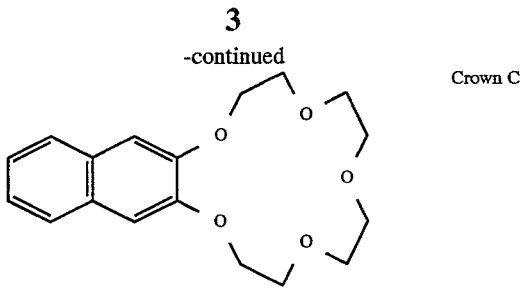

Crown C

Additional crown ethers which are suitable for use as ionophores in the present invention include dibenzo-18-crown-6; 18-crown-6; 15-crown-5; 21-crown-7; [2.2.2] cryptate; 12-crown-4; benzo-18-crown-6; decyl-18-crown-6; 2,6-dimethylpyridine-18-crown-6; 2,6-dimethylbenzoic acid-18-crown-6; sym-hydroxy-dibenzo-16-crown-5 and hydroxymethyl-18-crown-6; 1,10-diaza-18-crown-6; 2,2-bis [(12-crown-4)methoxycarbonyl]-octadecane and monoaza-18-crown-6-N-acetic acid.

One aspect of the present invention is directed to an analytical test strip for the detection of specific gravity in urine which strip comprises an absorbent carrier impregnated with a suitable polyelectrolyte polymer, indicator and crown ether. The absorbent carrier of the test strip is preferably filter paper. Other materials suitable as the absorbent carrier include felt, porous ceramic strips and woven or matted glass fibers such as those described in U.S. Pat. No. 3,846,247. Also suitable are wood, cloth, sponge material and argillaceous substances such as those described in U.S. Pat. No. 3,552,928. Alternatively, the absorbent carrier can be of a nonporous material such as a polymeric film or glass. In preparation of the strip it is impregnated with a solution of the crown ether in an organic solvent such as tetrahydrofuran (THF), toluene or ethanol. After drying, the strip is dipped into a second solution which is an aqueous solution of the polyelectrolyte. After drying, the strip is dipped a third time to apply the indicator which is typically applied from a mixture of a polar organic solvent and water. The following table sets out the preferred and allowable range of ingredients for preparing a 3 dip strip of this type in which the first organic solvent is THF, the polyelectrolyte is Gantrez®, the second organic solvent is isopropanol and the indicator is Bromo Thymol Blue (BTB).

| SG Reagent Composition. | | | |
|---|---|---|---|
| Ingredient | Function | Prefer Conc. used | Allowable Range |
| Crown application | | | |
| THF | Solvent | 1000 mL | — |
| Crown | Enhancer | 14.6 g | 1–30 g/L |
| Polyelectrolyte application | | | |
| Water | Solvent | 1000 mL | — |
| Gantrez | Active ingredient | 24.2 g | 6–75 g |
| pH | Titration | 7.6 | 5.0–8.3 |
| Indicator application | | | |
| Isopropanol | Solvent | 50 mL | — |
| Water | Solvent | 50 mL | — |
| Bromo Thymol Blue | Indicator dye | 1.0 g | 0.2–4.0 g |

The present invention is further illustrated by the following examples:

EXAMPLE I

Reagent strips used in this example were prepared as follows: Filter paper (204 grade from Alhstron) was saturated with crown ether and indicator solutions as shown in the table above and dried at 100° C. for 10 minutes after each saturation. The resultant reagent paper was assembled into reagent strips by applying double stick adhesive to the backside of the reagent strip and attaching it to a polystyrene handle. Formulations using crown A (dibenzo-16-crown-5-oxyacetic acid), crown B (dicyclohexano-16-crown-5-oxyacetic acid) and crown C (naphtho-15-crown-5) were prepared along with controls containing only BTB and BTB and Gantrez polymer. The strips prepared in this manner were dipped in water having a predetermined specific gravity of 1.000 and 1.025 and the color change (in terms of change in reflectance) was determined termined at 590 nm using a Clinitek®-200[+] reflectance spectrophotometer from Bayer Diagnostics 60 seconds after dipping. The results of this experiment are tabulated in Table 1.

TABLE 1

| Crowns added to the BTB Dye | | | | |
|---|---|---|---|---|
| | | % R at 590 nm | | |
| SG Formula | Crown g/L | 1,000 Mean(sd) | 1,025 Mean(sd) | Δ % R |
| BTB | | 42.8(9.5*) | 58.8(4.9*) | 16.0 |
| BTB and Gantrez | | 8.2(8.4*) | 29.8(4.1*) | 21.6 |
| BTB and Crown A | 0.15 | 63.1(1.5) | 67.9(1.4) | 4.8 |
| BTB and Crown B | 0.15 | 60.4(2.0) | 68.8(1.1) | 8.4 |
| BTB and Crown A | 20.0 | 74.5(1.3) | 73.5(1.6) | 1.0 |
| BTB and Crown B | 20.0 | 75.1(2.0) | 73.2(1.8) | 1.9 |
| BTB and Crown C | 20.0 | 74.3(2.9) | 73.8(1.1) | 1.5 |

Crown B at 20 g/L contained 0.0437 eq. of $CO_2H/L$, while current Gantrez contains 0.3067 eq. of $CO_2H/L$. SG 1.025 solutions made by adding 7.75 g NaCl to 250 mL of water.

Formulas with crown ethers and BTB did not exhibit significant cation response as indicated by the small Δ%R between the 1.000 SG and 1.025 SG test fluids. Since cation response is the color generated in the presence of salts, the significant reduction in cation response observed in the presence of crown ethers establishes that these crown ethers do not produce a change in pH when exposed to cations. Based on this, one would not expect crown ethers to increase the sensitivity of the specific gravity test because the crown ethers by themselves do not detect ions.

EXAMPLE II

The specific gravity reagent strips used in this experiment were prepared by sequential saturations of filter paper (204 grade from Ahlstrom). The first saturation was with a tetrahydrofuran (THF) mix containing the crown ether and a control formulation of THF without the crown ether being used. The second dip solutions were water containing 24.2 g/L of Gantrez polymer with the pH having been adjusted to 7.8 with 10N NaOH prior to addition of the polymer. The final saturation was a mix containing 1.0 g/L of bromothymol blue (BTB) in 50% isopropanol and 50% water. Formulations using crown A, crown B and crown C (previously described) were prepared. The strips prepared in this manner were dipped in distilled water (SG 1.000) and water having a predetermined specific gravity of 1.025 and the color change determined as before. The results of this experiment are summarized in Table 2:

TABLE 2

Crowns added to Gantrez and BTB Dye

| | | % R at 590 nm | | |
|---|---|---|---|---|
| SG Formula | Crown g/L | Mean(sd) @ SG 1,000 | Mean(sd) @ SG 1,025 | Δ % R |
| BTB | | 42.8(9.5*) | 58.8(4.9*) | 16.0 |
| BTB and Gantrez | | 8.2(8.4*) | 29.8(4.1*) | 21.6 |
| BTB.Gantrez and Crown A | 0.2 | 6.5(0.6) | 29.9(1.2) | 23.4 |
| BTB.Gantrez and Crown A | 0.15 | 9.6(2.7) | 45.7(3.0) | 36.1 |
| BTB.Gantrez and Crown A | 5.0 | 16.5(9.1*) | 57.8(2.0*) | 41.3 |
| BTB.Gantrez and Crown A | 20.0 | 65.9(4.4) | 76.7(1.1) | 10.8 |
| BTB.Gantrez and Crown A | 0.2 | 7.5(0.6) | 33.6(1.3) | 26.2 |
| BTB.Gantrez and Crown B | 2.0 | 6.4(4.5) | 43.6(1.1) | 37.2 |
| BTB.Gantrez and Crown B | 5.0 | 12.7(1.5) | 51.8(2.5) | 39.1 |
| BTB.Gantrez and Crown B | 10.0 | 13.9(4.3) | 60.4(1.8) | 46.5 |
| BTB.Gantrez and Crown C | 0.2 | 9.7(1.1) | 31.1(0.9) | 21.4 |
| BTB.Gantrez and Crown C | 2.0 | 14.8(3.2) | 59.0(2.4) | 44.2 |
| BTB.Gantrez and Crown C | 5.0 | 31.8(2.5) | 62.6(1.4) | 30.8 |
| BTB.Gantrez and Crown C | 10.0 | 37.5(9.1) | 63.9(0.9) | 26.4 |

*Standard deviation of three batches of reagent made on separate days. All other standard deviations are of one batch of reagent. SG 1.025 solutions made by adding 7.75 g NaCl to 250 mL of water.

From Table 2, it can be determined that the %R @ 590 nm observed at SG of 1.025 increased with increasing crown ether concentration. The greatest difference between 1.000 and 1.025 SG samples was observed between 2 to 10 g/L of the crown ether. Optimal formulas with crown ether, Gantrez polymer and BTB dye produced up to a 47% R difference between fluid having a specific gravity of 1.000 and the 1.025 specific gravity fluid. Both ionizable (crown A+B) and neutral ionophores (crown C) increased the cation response.

The resulting increased cation response observed upon the addition of crown ethers to the reagent containing Gantrez and BTB was unexpected because crowns A, B and C reduced cation response when measured with BTB but without Gantrez. The addition of excess crown ether A (>20 g/L) reduced the cation response. This demonstrates that an optimal concentration must be established for each crown ether used. In the case of crown A this would be about 5.0 g/L. The optimal concentration in the dip solution of crown B would be about 10.0 g/L and crown C would be about 2.0 g/L. This increased cation response is desirable because of improved test accuracy, as indicated by the greater Δ%R between the SG 1.000 and SG 1.025 test samples without an increase in variability.

In Table 3 there are presented data which illustrate the standard curve which can be obtained when crown ethers are added to standard formulations containing Gantrez and BTB dye.

TABLE 3

Standard Curve for Crowns Added to Gantrez and BTB Dye

| | % R @ 590 nm for Current SG Formula With | |
|---|---|---|
| SG | No Crown | Crown C at 2.0 g/L |
| 1.000 | 6.00 | 12.50 |
| 1.005 | 7.15 | 19.40 |
| 1.010 | 9.02 | 29.03 |
| 1.015 | 12.35 | 47.72 |
| 1.020 | 17.25 | 52.07 |
| 1.025 | 28.20 | 60.50 |

From Table 3 it is apparent that the signal is proportional to the specific gravity of the test sample and that the proprotionality is consistent between formulations with and without crown ether addition. In each case the signal (in terms of %R) is greater with the reagent containing the crown ether than that which is without.

What is claimed is:

1. In a method for determining the specific gravity of a fluid test sample which method comprises combining the test sample with an acidic or basic polyelectrolyte polymer which is at least about 50 percent neutralized and a pH indicator capable of producing a detectable response based on interaction between the polyelectrolyte and the fluid test sample, the improvement which comprises introducing a crown ether ionophore into the combination of fluid sample, polymer and indicator.

2. The method of claim 1 wherein the crown ether is dibenzo-16-crown-5-oxyacetic acid; dicyclohexano-16-crown-5-oxyacetic acid; naptho-15-crown-5; dibenzo-18-crown-6; 18-crown-6; 15-crown-5; 21-crown-7; [2.2.2] cryptate; 12-crown-4; benzo-18-crown-6; decyl-18-crown-6; 2,6-dimethyl pyridine-18-crown-6; 2,6-dimethylbenzoic acid-18-crown-6; sym-hydroxy-dibenzo-16-crown-5 hydroxymethyl-18-crown-6; 1,10-diaza-18-crown-6; 2,2-bis [(12-crown-4)-methoxycarbonyl]-octadecane or monoaza-18-crown-6-N-acetic acid.

3. The method of claim 2 wherein the crown ether is dibenzo-16-crown-5-oxyacetic acid; dicyclohexano-16-crown-5-oxyacetic acid or naptho-15-crown-5.

4. The method of claim 1 wherein the polyelectrolyte polymer is weakly basic or acidic.

5. The method of claim 1 wherein the fluid test sample is urine.

6. The method of claim 1 wherein the pH indicator is bromo thymol blue.

7. The method of claim 1 wherein the polyelectrolyte polymer is a maleic anhydride/methylvinylether.

8. A test device for the determination of the specific gravity of a fluid test sample which comprises an absorbant carrier having absorbed therein an acidic or basic polyelectrolyte polymer which is at least about 50 percent neutralized, a pH indicator capable of producing a detectable response based on interaction between the polyelectrolyte polymer and the fluid test sample and a crown ether ionophore.

9. The device of claim 8 wherein the absorbant carrier is filter paper.

10. The device of claim 8 wherein the polyelectrolyte polymer is weakly basic or acidic.

11. The device of claim 8 wherein the crown ether is dibenzo-16-crown-5-oxyacetic acid, dicyclohexano-16-crown-5-oxyacetic acid or naptho-15-crown-5.

12. A test strip for the determination of the specific gravity of urine which comprises filter paper having absorbed therein a maleic anhydride/methylvinylether polyelectrolyte which is at least about 50 percent neutralized, bromo thyoml blue and a crown ether ionophore selected from the group consisting of dibenzo-16-crown-5-oxyacetic acid, dicyclohexano-16-crown-5-oxyacetic acid and naptho-15-crown-5.

* * * * *